(12) United States Patent
Rubinstein et al.

(10) Patent No.: US 7,590,437 B2
(45) Date of Patent: *Sep. 15, 2009

(54) MEASUREMENT OF CARDIAC OUTPUT AND BLOOD VOLUME BY NON-INVASIVE DETECTION OF INDICATOR DILUTION

(75) Inventors: Eduardo H. Rubinstein, Santa Monica, CA (US); Oscar V. Scremin, Los Angeles, CA (US); Daniel P. Holschneider, Los Angeles, CA (US); Jean-Michel I. Maarek, Rancho Palos Verdes, CA (US)

(73) Assignee: Alfred E. Mann Institute for Biomedical Engineering at the University of Southern California, Los Angeles, CA (US)

( * ) Notice: Subject to any disclaimer, the term of this patent is extended or adjusted under 35 U.S.C. 154(b) by 348 days.

This patent is subject to a terminal disclaimer.

(21) Appl. No.: 10/847,480

(22) Filed: May 17, 2004

(65) Prior Publication Data
US 2004/0215093 A1 Oct. 28, 2004

Related U.S. Application Data

(63) Continuation of application No. 10/153,387, filed on May 21, 2002, now Pat. No. 6,757,554.
(60) Provisional application No. 60/292,580, filed on May 21, 2001.

(51) Int. Cl.
*A61B 5/00* (2006.01)
(52) U.S. Cl. .................................................... 600/317
(58) Field of Classification Search ................ 600/310, 600/317, 504, 431, 410, 420, 318, 479, 321, 600/340, 324, 454, 459; 424/9.1, 1.11, 9.6; 356/28
See application file for complete search history.

(56) References Cited

U.S. PATENT DOCUMENTS

| 4,303,336 A | 12/1981 | Cullis |
| 4,326,539 A | 4/1982 | Obermajer |
| 5,331,958 A | 7/1994 | Oppenheimer |
| 5,685,989 A | 11/1997 | Krivitski |
| 5,687,726 A | 11/1997 | Hoeft |
| 5,766,125 A | 6/1998 | Aoyagi et al. |
| 5,797,396 A | 8/1998 | Geiser et al. |
| 5,999,841 A | 12/1999 | Aoyagi et al. |
| 6,041,246 A | 3/2000 | Krivitski et al. |
| 6,159,445 A | 12/2000 | Klaveness et al. |

(Continued)

OTHER PUBLICATIONS

Darovic, G.O. Hemodynamic monitoring. Chapter 11: Monitoring cardiac output. 1995. pp. 327-346. 2d Ed. W.B. Saunders.

(Continued)

*Primary Examiner*—Max Hindenburg
*Assistant Examiner*—Brian Szmal
(74) *Attorney, Agent, or Firm*—McDermott Will & Emery LLP

(57) ABSTRACT

A system for evaluating the cardiovascular system parameters using indicator dilution and non-invasive or minimally invasive detection methods is disclosed. Intravascular indicators are stimulated, and emissions patterns detected for computation of cardiac output, cardiac index, blood volume and other indicators of cardiovascular health.

33 Claims, 6 Drawing Sheets

U.S. PATENT DOCUMENTS

| | | | |
|---|---|---|---|
| 6,169,914 B1 * | 1/2001 | Hovland et al. | 600/340 |
| 6,178,340 B1 | 1/2001 | Svetliza | |
| 6,223,069 B1 * | 4/2001 | Pfeiffer et al. | 600/431 |
| 6,228,344 B1 * | 5/2001 | Dorshow et al. | 424/9.1 |
| 6,230,035 B1 | 5/2001 | Aoyagi et al. | |
| 6,280,386 B1 | 8/2001 | Alfano et al. | |
| 6,280,703 B1 | 8/2001 | Combs et al. | |
| 6,299,583 B1 | 10/2001 | Eggers et al. | |
| 6,424,857 B1 | 7/2002 | Henrichs et al. | |
| 6,493,567 B1 | 12/2002 | Krivitski et al. | |
| 6,542,769 B2 * | 4/2003 | Schwamm et al. | 600/420 |
| 6,554,775 B1 | 4/2003 | Peyman et al. | |
| 6,718,190 B2 | 4/2004 | Krivitski et al. | |
| 6,746,407 B2 | 6/2004 | Steuer et al. | |
| 6,746,415 B1 | 6/2004 | Steuer et al. | |
| 6,757,554 B2 * | 6/2004 | Rubinstein et al. | 600/317 |
| 7,261,696 B2 | 8/2007 | Krivitski | |
| 2003/0060722 A1 | 3/2003 | Pfeiffer | |

OTHER PUBLICATIONS

Desmettre, T. et al. Fluorescence properties and metabolic features of indocyanine green (ICG) as related to angiography. Survey of opthalmology. Jul.-Aug. 2000. pp. 15-27. vol. 45, No. 1.

Dorshow. R.B. et al. Noninvasive fluorescence detection of hepatic and renal function. Journal of biomedical optics. Jul. 1998. pp. 340-345. vol. 3, No. 3.

Fok et al. Oxygen consumption by lungs with acute and chronic injury in a rabbit model. Intensive care medicine. 2001. pp. 1532-1538. vol. 27.

Geddes, L.A. Cardiovascular devices and their applications. Chapter 4: The measurement of cardiac output and blood flow. 1984. pp. 101-120. John Wiley & Sons, New York.

Hollins, B. et al. Fluorometric determination of indocyanine green in plasma. Clinical chemistry. 1987. pp. 765-768. vol. 33, No. 6.

Nihon Kohden. website: http://kohden.co.jp/intl/ppms-ddg2001.html. Website viewed May 17, 2001.

Preckel, B. et al. Effect of dantrolene in an in vivo and in vitro model of myocardial reperfusion injury. Acta Anaesthesiol Scand. 2000. pp. 194-201. vol. 44.

Sakka, G. et al. Comparison of Cardiac Output and Circulatory Blood Volumes by Transpulmonary Thermo-dye Dilution and Transcutaneous Indocyanine Green Measurement in Critically Ill Patients. Feb. 2002. pp. 559-565.Chest vol. 121 Issue 2.

International Search Report for PCT Application Serial No. PCT/US07/15650, mailed on Aug. 20, 2008.

* cited by examiner

MEASUREMENT OF CARDIAC OUTPUT AND BLOOD VOLUME BY NON-INVASIVE DETECTION OF INDICATOR DILUTION

CROSS-REFERENCE TO RELATED APPLICATIONS

This application is a continuation of U.S. patent application Ser. No. 10/153,387, filed May 21, 2002, now U.S. Pat. No. 6,757,554, issued Jun. 29, 2004, and entitled "Measurement of Cardiac Output and Blood Volume by Non-Invasive Detection of Indicator Dilution," which claims priority to U.S. Provisional Application Ser. No. 60/292,580, filed May 21, 2001, entitled Method and Apparatus for Measurement of Cardiac Output by Transcutaneous Detection of Fluorescent Indicator. The content of both applications is incorporated herein by reference.

BACKGROUND OF THE INVENTION

1. Field of the Invention

This invention pertains to the detection of parameters of cardiovascular system of a subject.

2. General Background and State of the Art

Cardiac output is a central part of the hemodynamic assessment in patients having heart disease, acute hemodynamic compromise or undergoing cardiac surgery, for example. Cardiac output is a measure of the heart's effectiveness at circulating blood throughout the circulatory system. Specifically, cardiac output (measured in L/min) is the volume of blood expelled by the heart per beat (stroke volume) multiplied by the heart rate at the. An abnormal cardiac output is at least one indicator of cardiovascular disease.

The current standard method for measuring cardiac output is the thermodilution technique (Darovic, G. O. Hemodynamic monitoring: invasive and noninvasive clinical application. 2nd Ed. W. B. Saunders, 1995). Generally, the technique involves injecting a thermal indicator (cold or heat) into the right side of the heart and detecting a change in temperature caused as the indicator flows into the pulmonary artery.

Typically, the thermodilution technique involves inserting a flow-directed balloon catheter (such as a Swan-Ganz catheter) into a central vein (basilic, internal jugular or subclavian) and guiding it through the right atrium and ventricle to the pulmonary artery. The balloon catheter is typically equipped with a thermistor near its tip for detecting changes in blood temperature. A rapid injection of a bolus of chilled glucose solution (through a port in the catheter located in the vena cava near the right atrium) results in a temperature change in the pulmonary artery detected with the thermistor. The measured temperature change is analyzed with an external electronic device to compute the cardiac output. The algorithm implemented in this computation is typically a variant of the Stewart-Hamilton technique and is based on the theory of indicator mixing in stirred flowing media (Geddes L A, Cardiovascular devices and measurements. John Wiley & Sons. 1984).

Thermodilution measurements of cardiac output are disadvantageous for several reasons. First, thermodilution is an expensive and invasive technique requiring performance in a sterile surgical suite. Second, this procedure has severe risks to the patient such as local infections, septicemia, bleeding, embolization, catheter-induced damage of the carotid, subclavian and pulmonary arteries, catheter retention, pneumothorax, dysrrhythmias including ventricular fibrillation, perforation of the atrium or ventricle, tamponade, damage to the tricuspid values, knotting of the catheter, catheter transection and endocarditis. Third, only specially-trained surgeons can insert the balloon catheter for thermodilution cardiac output. Last, thermodilution measurements of the cardiac output are too invasive to be performed in small children and infants.

Another method used for measuring cardiac output is the dye indicator dilution technique. In this technique, a known volume and concentration of indicator is injected into the circulatory flow. At a downstream point, a blood sample is removed and the concentration of the indicator determined. The indicator concentration typically peaks rapidly due to first pass mixing of the indicator and then decreases rapidly as mixing proceeds in the total blood volume (~10 seconds; first pass concentration curve). Further, indicator concentration slowly diminishes as the indicator is metabolized and removed from the circulatory system by the liver and/or kidneys (time depending upon the indicator used). Thus, a concentration curve can be developed reflecting the concentration of the indicator over time. The theory of indicator dilution predicts that the area under the first pass concentration curve is inversely proportional to the cardiac output.

Historically, indicator dilution techniques have involved injecting a bolus of inert dye (such as indocyanine green) into a vein and removing blood samples to detect the concentration of dye in the blood over time. For example, blood samples are withdrawn from a peripheral artery at a constant rate with a pump. The blood samples are passed into an optical sensing cell in which the concentration of dye in the blood is measured. The measurement of dye concentration is based on changes in optical absorbance of the blood sample at several wavelengths.

Dye-dilution measurements of cardiac output have been found to be disadvantageous for several reasons. First, the necessity for continuous arterial blood withdrawal are time consuming, labor intensive and deplete the patient of valuable blood. Second, the instruments used to measure dye concentrations (densitometer) must be calibrated with samples of the patient's own blood containing known concentrations of the dye. This calibration process can be very laborious and time consuming in the context of the laboratory where several samples must be run on a daily basis. Further, technical difficulties arise in extracting the dye concentration from the optical absorbance measurements of the blood samples.

A variation on the dye-dilution technique is implimented in the Nihon Kohden pulse dye densitometer. In this technique, blood absorbance changes are detected through the skin with an optical probe using a variation of pulse oximetry principles. This variation improves on the prior technique by eliminating the necessity for repeated blood withdrawal. However, as described above, this technique remains limited by the difficulty of separating absorbance changes due to the dye concentration changes from absorbance changes due to changes in blood oxygen saturation or blood content in the volume of tissue interrogated by the optical probe. This method is also expensive in requiring large amounts of dye to create noticeable changes in absorbance and a light source producing two different wavelengths of light for measuring light absorption by the dye and hemoglobin differentially. Even so, the high background levels of absorption in the circulatory system makes this technique inaccurate. Finally, where repeat measurements are desired, long intervals must ensue for the high levels of the indicator to clear from the blood stream. Thus, this technique is inconvenient for patients undergoing testing and practitioners awaiting results to begin or alter treatment.

Other approaches for measuring cardiac output exist which are not based on indicator dilution principles. These include ultrasound Doppler, ultrasound imaging, the Fick principle applied to oxygen consumption or carbon dioxide production and electric impedance plethysmography (Darovic, supra). However, these techniques have specific limitations. For instance, the ultrasound techniques (Doppler and imaging) require assumptions on the three-dimensional shape of the imaged structures to produce cardiac output values from velocity or dimension measurements.

Blood volume measures the amount of blood present in the cardiovascular system. Blood volume is also a diagnostic measure which is relevant to assessing the health of a patient. In many situations, such as during or after surgery, traumatic accident or in disease states, it is desirable to restore a patient's blood volume to normal as quickly as possible. Blood volume has typically been measured indirectly by evaluating multiple parameters (such as blood pressure, hematocrit, etc.). However, these measures are not as accurate or reliable as direct methods of measuring blood volume.

Blood volume has been directly measured using indicator dilution techniques (Geddes, supra). Briefly, a known amount of an indicator is injected into the circulatory system. After injection, a period of time is allowed to pass such that the indicator is distributed throughout the blood, but without clearance of the indicator from the body. After the equilibration period, a blood sample is drawn which contains the indicator diluted within the blood. The blood volume can then be calculated by dividing the amount of indicator injected by the concentration of indicator in the blood sample (for a more detailed description see U.S. Pat. No. 6,299,583 incorporated by reference). However, to date, the dilution techniques for determining blood volume are disadvantageous because they are limited to infrequent measurement due to the use of indicators that clear slowly from the blood.

Thus, it would be desirable to have a non-invasive, cost effective, accurate and sensitive technique for measuring cardiovascular parameters, such as cardiac output and blood volume.

INVENTION SUMMARY

The present invention is directed to methods and systems for assessing cardiovascular parameters within the circulatory system using indicator dilution techniques. Cardiovascular parameters are any measures of the function or health of a subjects cardiovascular system.

In one aspect of the invention, a non-invasive method for determining cardiovascular parameters is described. In particular, a non-invasive fluorescent dye indicator dilution method is used to evaluate cardiovascular parameters. Preferably, the method is minimally invasive requiring only a single peripheral, intravenous line for indicator injection into the circulatory system of the patient. Further, it is preferable that only a single blood draw from the circulatory system of the patient be taken for calibration of the system, if necessary. Further, cardiovascular parameters may be evaluated by measuring physiological parameters relevant to assessing the function of the heart and circulatory system. Such parameters include, but are not limited to cardiac output and blood volume.

Such minimally invasive procedures are advantageous over other methods of evaluating the cardiovascular system. First, complications and patient discomfort caused by the procedures are reduced. Second, such practical and minimally invasive procedures are within the technical ability of most doctors and nursing staff, thus, specialized training is not required. Third, this minimally invasive methods may be performed at a patient's bedside or on an out-patient basis. Finally, methods may be used on a broader patient population, including patients whose low risk factors may not justify the use of central arterial measurements of cardiovascular parameters.

In another aspect of the invention, these methods may be utilized to evaluate the cardiovascular parameters of a patient at a given moment in time, or repeatedly over a selected period of time. Preferably, the dosages of indicators and other aspects of the method can be selected such that rapid, serial measurements of cardiovascular parameters may be made. These methods can be well suited to monitoring patients having cardiac insufficiency or being exposed to pharmacological intervention over time. Further, the non-invasive methods may be used to evaluate a patient's cardiovascular parameters in a basal state and when the patient is exposed to conditions which may alter some cardiovascular parameters. Such conditions may include, but are not limited to changes in physical or emotional conditions, exposure to biologically active agents or surgery.

In another aspect of the invention, modifications of the method may be undertaken to improve the measurement of cardiovascular parameters. Such modifications may include altering the placement of a photodetector relative to the patient or increasing blood flow to the detection area of the patient's body.

In another aspect of the invention, the non-invasive method of assessing cardiovascular parameters utilizes detection of indicator emission, that is fluorescence, as opposed to indicator absorption. Further, indicator emissions may be detected in a transmission mode and/or reflection mode such that a broader range of patient tissues may serve as detection sites for evaluating cardiovascular parameters, as compared to other methods. Preferably, measurement of indicator emission are more accurate than measurements obtained by other methods, as indicator emission can be detected directly and independent of the absorption properties of whole blood.

In another aspect of the invention, a system for the non-invasive or minimally invasive assessment of cardiovascular parameters is described. In particular, such a system may include an illumination source for exciting the indicator, a photodetector for sensing emissions of electromagnetic radiation from the indicator and a computing system for receiving emissions data, tracking data over time and calculating cardiovascular parameters using the data.

In another aspect of the invention, the methods and system described herein may be used to assess cardiovascular parameters of a variety of subjects. In some embodiments, the methodology can be modified to examine animals or animal models of cardiovascular disease, such as cardiomyopathies. The methodology of the present invention is advantageous for studying animals, such as transgenic rodents whose small size prohibits the use of current methods using invasive procedures. The present invention is also advantageous in not requiring anesthesia which can effect cardiac output measurements.

In other embodiments, the methodology can be modified for clinical application to human patients. The present invention may be used on all human subjects, including adults, juveniles, children and neonates. The present invention is especially well suited for application to children, and particularly neonates. As above, the present technique is advantageous over other methods at least in that it is not limited in application by the size constraints of the miniaturized vasculature relative to adult subjects.

DETAILED DESCRIPTION OF THE PREFERRED EMBODIMENTS

The method and system of the present invention are for the evaluation of cardiovascular parameters of a subject using an indicator dilution technique.

Figure 9:
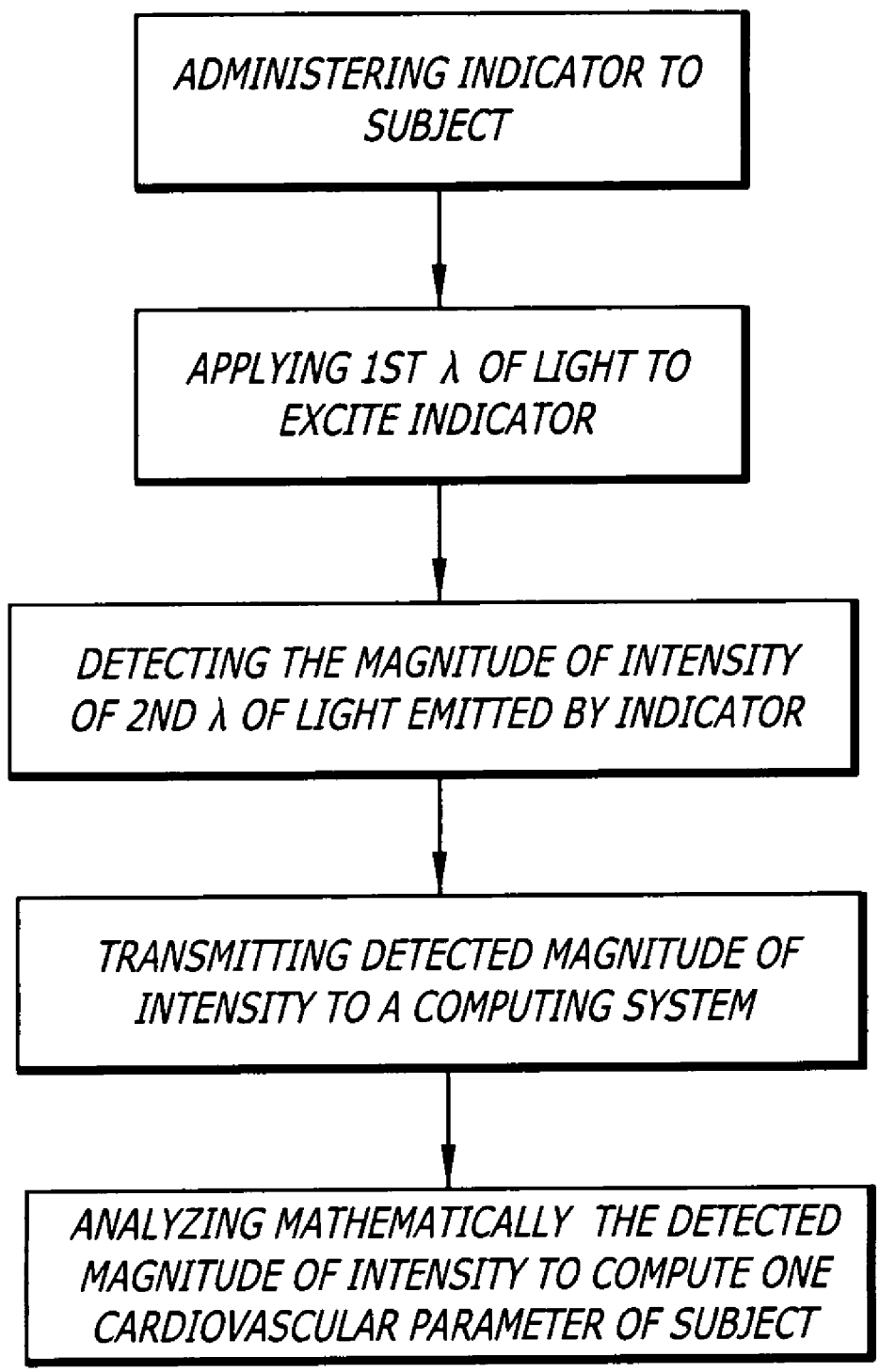
FIG. 9 is a flow chart depicting one method of the present invention.

The method of this invention generally involves the injection of a selected amount of indicator into the bloodstream of the subject (FIG. 9). Preferably, the indicator is illuminated using a first wavelength of excitation light selected cause the indicator to fluoresce and emit a second wavelength of light. A photodetector is placed near the subject for the detection of the intensity of the second wavelength of emitted light which is proportional to the concentration of the indicator circulating within the circulatory system. The photodetector transmits this intensity information to a computing system, which records and preferably maps the intensity curve of the indicator detected over time.

Typically, the indicator concentration values increase to a peak rapidly after injection of the indicator. Then, the concentration values decrease rapidly, then more steadily as the indicator is diffused throughout the body and metabolized over time. A microprocessor driven computation then can calculate from the concentration curve, the patient's cardiac output and/or blood volume values. Additionally, values can be generalized repeatedly using this method, at intervals of about every 1-2 minutes.

Indicators. The indicators useful in this in invention are preferably inert and biocompatible in that they do not alter cardiovascular parameters, such as heart rate. Further, the indicator is preferably a substance that once injected, does not diffuse out of the vasculature of the cardiovascular system. Also, the indicator is preferably selected to be one which is metabolized within the body at a rate such that repeated measures using this method may be conducted at intervals of about 1-2 minutes. It is also desirable that the background levels of circulating indicator be cleared between intervals, although measurements may be taken when background levels are not zero. Finally, the indicator can be selected to be detectable by the photodetector system selected.

In one embodiment, a non-invasive dye indicator dilution method may be used to evaluate cardiovascular function function. Many different dye indicators may be used within the scope of this invention. Preferably, the dye indicator is fluorescent having an excitation wavelength and an emission wavelength in the near infrared spectrum, preferably about 750 nm to about 1000 nm, and more preferably about 750 nm to about 850 nm.

Most preferably, the indicator used is indocyanine green (ICG; purchased for example from Akorn, Decatur or Sigma, St. Louis, Mo.; commercial names: Diagnogreen©, ICGreen©, Infracyanine©, Pulsion©). ICG has been previously been used to study the microcirculation of the eye, the digestive system and liver function (Desmettre, T., J. M. Devoisselle, and S. Mordon. Fluorescence properties and metabolic features of indocyanine green (ICG) as related to angiography. Surv Ophthalmol 45, 15-27, 2000). ICG fluoresces intensely when excited at near infrared wavelengths. In the context of this invention, ICG in blood plasma has a peak fluorescence of about 810 to 830±10 nm with an optimal excitation wavelength of about 780 nm (Hollins, supra; Dorshow, supra). ICG may be advantageous for use in this invention in remains intravascular because it is protein bound. ICG breaks down quickly in aqueous solution, and metabolites are not fluorescent, minimizing recirculation artifact and reducing the time period between which measurements can be made. The wavelength of emission of ICG is also within the optical window (750-1000 nm) in which living tissues are relatively transparent to light.

Other biocompatible fluorescent dyes such as fluorescein and rhodamine would also be suitable in this invention. Fluorescein in blood plasma has a peak fluorescence of about 518±10 nm with an optimal excitation wavelength of about 488 nm (Hollins, supra; Dorshow, supra). Rhodamine in blood plasma has a peak fluorescence of about 640±10 nm with an optimal excitation wavelength of about 510 nm.

Indicator dosage. The dosage of indicator is preferably selected such that an amount used is non-toxic to the subject, is present in the circulatory system for an amount of time adequate to establish an indicator concentration curve, but is metabolized in an amount of time such that repeated measurements can be conducted at intervals of about 1-2 minutes apart. Further, the indicator is preferably administered to the subject by injection into a vein.

A dosage of about 0.005 mg/kg is preferable in that this dose leads to peak blood concentrations below 0.001 mg/ml. In this concentration range, the measurement of the circulating indicator concentration is linearly related to the intensity of the emission wavelength detected. For example, in a laboratory animal model, about 0.015 mg can be injected into a 3 kg rabbit (blood volume=200 ml) such that the average circulating concentration is about 0.000075 mg/ml whole blood.

Dye dilution techniques have been applied in humans in other using indocyanine green as a dye. Living tissues of humans and animals are relatively transparent for near infrared wavelengths of light which allows for transmission of light across several mm of tissue and transcutaneous detection of the fluorescence emission of ICG. The use of dosages in the ranges stated above is additionally suitable for human use.

Illumination Source. The illumination sources useful in this invention are preferably selected to produce an excitation wavelength in the near infrared spectrum, preferably about 750 nm to about 1000 nm, and more preferably about 750 to about 850 nm. This selection is advantageous in at least that most tissues are relatively transparent to wavelengths in this range. Thus, in some embodiments, an indicator in the blood stream is excitable transcutaneously and indicator emissions detected transcutaneously. Further, blood constituents do not fluoresce at these wavelengths, thus there is no other contributor to the measured fluorescence emission signal. Therefore, this method is advantageous in that at least the sensitivity of detection in this method is improved over other methods which measure indicator absorption, as opposed to emission.

However, it is within the scope of the invention to use other wavelengths of light, for example in the blue-green or ultraviolet range as some tissues are relatively transparent even at these wavelengths. Selection of the illumination source, therefore, can depend in part on the indicator selected and the tissue from which detection will be made. Preferably, the illumination source is selected to result in the peak emission wavelength of the indicator.

Examples of illumination sources which may be used in this invention include, but are not limited to lamps, light emitting diodes (LEDs), lasers or diode lasers.

In some embodiments, modifications to the system or illumination source may be altered to further to maximize the sensitivity or accuracy of the system for measuring indicator concentration. For example, in some embodiments, the excitation wavelength produced by the illumination source will be steady. Alternatively, the excitation wavelength produced by the illumination source can be modulated using a locking detection technique.

For example, the illumination source may emit light in a periodic varying pattern having a fixed frequency and the emissions recorded by the photodetector read at the same frequency to improve the accuracy of the readings. The periodic varying pattern and frequency can be selected to improve noise-rejection and should be selected to be compatible with the rest of the instrumentation (such as the light source and photodetector).

The illumination source may be adapted to target a detection area of the subject's tissue from which emission wavelength intensity will be recorded. In some embodiments, the illumination source may comprise an optic fiber for directing the excitation light to the detection area. In some embodiments, the illumination source may comprise mirrors, filters and/or lenses for directing the excitation light to the detection area.

Detection Areas. The target detection area is that location of a subject's tissue which is exposed to the excitation wavelength of light and/or from which the emission wavelength light intensity output will be measured.

Preferably, the method of detection is non-invasive. In these embodiments, a detection area is selected such that a photodetector can be placed in proximity to the detection area and emission wavelength light intensity measured. Preferably, the photodetector is placed transdermally to at least one blood vessel, but more preferably a highly vascularized tissue area. Examples of detection areas include, but are not limited to fingers, auricles of the ears, nostrils and areas having non-kertanized epithelium (such as the nasal mucosa or inner cheek). In alternative embodiments, the method of detection is minimally invasive. For example, the photodetector can be placed subdermally (within or beneath the epidermis) and proximate to at least one blood vessel or in a perivascular position. In yet alternative embodiments, the method of detection is invasive. For example, the photodetector can be placed intravascularly to detect indicator emissions, such as within an artery.

Additionally, the detection area may be arterialized during indicator emission detection. Examples of conditions resulting in detection area arterialization include, but are not limited to heating or exposure to biologically active agents which effect sympathetic system blockade (such as lidocaine).

Photodector. The detection of indicator emissions can be achieved by optical methods known in the art. Measurement of indicator concentration can be made by administering a detectable amount of a dye indicator and using a non-invasive, minimally invasive or intravascular procedures, preferably for continuous detection. Preferably, the photodetector is positioned proximately to the detection area of the subject. The photodetector may be positioned distally or proximately to the site of the illumination source.

In some embodiments, fluorescent light is emitted from the indicator with the same intensity for all directions (isotropy). Consequently, the emission of the dye can be detected both in "transmission mode" when the excitation light and the photodetector are on opposite sides of the illuminated tissue or in "reflection mode" when the excitation and the photodetector are on the same side of the tissue. This is advantageous over other methods at least in that the excitation light and emitted light can be input and detected from any site on the body surface and not only optically thin structures.

Photodetectors which are useful in this invention are those selected to detect the quantities and light wavelengths (electromagnetic radiation) emitted from the selected indicator. Photodectors having sensitivity to various ranges of wavelengths of light are well known in the art.

In some embodiments, modifications to the system are made to further enhance the sensitivity or accuracy of the system for measuring indicator concentration. For example in some embodiments, the detection system can incorporate a lock-in detection technique. For example, a lock-in amplifier can be used to modulate the source of light emission at a specific frequency and to amplify the output of the photodetector only at that frequency. This feature is advantageous in at least that it further improves the sensitivity of the system by reducing signal to noise and allows detection of very small amounts of fluorescence emission.

In some embodiments a photomultiplier tube is utilized as or operably connected with another photodetector to enhance the sensitivity of the system. Finally, in some embodiments, additional features, such as filters, may be utilized to minimize the background of the emission signals detected. For example, a filter may be selected which corresponds to the peak wavelength range or around the peak wavelength range of the indicator emission.

The detected electromagnetic radiation is converted into electrical signals by a photoelectric transducing device which is integral to or independent of the photodetector. These electrical signals are transmitted to a microprocessor which records the intensity of the indicator emissions as correlated to the electrical signal for any one time point or over time. (For an example of such a device see U.S. Pat. No. 5,766,125, herein incorporated by reference.)

System Calibration. Preferably, the method is further minimally invasive in requiring only a single peripheral blood draw from the circulatory system be taken for calibration purposes. In this invention, indicator concentration is preferably being measured continuously and non-invasively using a photodetector. However, one blood sample from the subject may be withdrawn for calibration of the actual levels of circulating indicator with the indicator levels detected by the system. For example, a blood sample may be drawn from the subject at a selected time period after the administration of the indicator into the blood stream. The blood sample may then be evaluated for the concentration of indicator present by comparison with a calibration panel of samples having known indicator concentrations. Evaluation of the indicator concentration may be made spectrophotometrically or by any other means known in the art. Where the subject blood concentration of indicator falls within a range of about 0.001 to about 0.002 mg/ml, the concentration-fluorescence curve is linear and it crosses the origin of the axes, that is the fluorescence is zero when the concentration is zero. Therefore a single measurement point suffices to define the calibration curve, and no further blood samples need be taken.

More preferably no blood draw is required for calibration of this system. It is noted that the fluorescence of some indicators, such as ICG, does not substantially vary from patient to patient and that the skin characteristics are relatively constant for large classes of patients. Thus, the fluorescence in the blood of the patient measured from a given site on the body surface can be converted in an absolute measurement of ICG concentration, once the curve of indicator concentration vs. fluorescence is defined for that site of measurement.

This method and system may be utilized to measure several cardiovascular parameters. Once the system has been calibrated to the subject (where necessary) and the indicator emissions detected and recorded over time, the computing system may be used to calculate cardiovascular parameters including cardiac output and blood volume.

Cardiac output calculations. In some embodiments, the cardiac output is calculated using equations which inversely correlate the area under the first pass indicator emission curve (magnitude of intensity curve) with cardiac output. Cardiac output is typically expressed as averages (L/min). The general methods have been previously described (Geddes, supra, herein incorporated by reference).

Classically, the descending limb of the curve is plotted semilogrithmically to identify the end of the first pass of indicator. For example, the descending limb of the curve may be extrapolated down to 1% of the maximum height of the curve. The curve can then be completed by plotting values for times preceding the end time. Finally, the area under this corrected curve is established and divided by the length (time) to render a mean height. This mean height is converted to mean concentration after calibration of the detector. The narrower the curve, the higher the cardiac output; the wider the curve, the lower the cardiac output. Several variations of this calculation method are found, including methods that fit a model equation to the ascending and descending portions of the indicator concentration curve.

Depending upon the indicator type and dosage selected, the curve may not return to zero after the end of the first pass due to a residual concentration of indicator recirculating in the system. Subsequent calculations of cardiac output from the curve may then account for this recirculation artifact by correcting for the background emissions, prior to calculating the area under the curve. This system is advantageous over the known methods in that at least the emission magnitude of intensity is being directly measured and no measurement of hemoglobin nor accommodation for hemoglobin absorbance or need be made.

Results obtained using this system can be normalized for comparison between subjects by expressing cardiac output as a function of weight (CO/body weight (L/min/kg)) or as a function of surface area (cardiac index=CO/body surface area (L/min/m$^2$)).

Blood volume calculations. In some embodiments, blood volume may be measured independently or in addition to the cardiac output. General methods of measuring blood volume are known in the art. In some embodiments, circulating blood volume may be measured using a low dose of indicator which is allowed to mix within the circulatory system for a period of time selected for adequate mixing, but inadequate or the indicator to be completely metabolized. The circulating blood volume may then be calculated by back extrapolating to the instant of injection the slow metabolic disappearance phase of the concentration curve detected over time (Bloomfield, D. A. Dye curves: The theory and practice of indicator dilution. University Park Press, 1974). Alternative methods of calculation include, but are not limited to those described in U.S. Pat. Nos. 5,999,841, 6,230,035 or 5,776,125, herein incorporated by reference.

This method and system may be used to examine the general cardiovascular health of a subject. In one embodiment, the method may be undertaken one time, such that one cardiac output and or blood volume measurement would be obtained. In other embodiments, the method may be undertaken to obtain repeated or continuous measurements of cardiovascular parameters over time. Further, repeated measures may be taken in conditions where the cardiovascular system is challenged such that a subject's basal and challenged cardiovascular parameters can be compared. Challenges which may be utilized to alter the cardiovascular system include, but are not limited to exercise, treatment with biologically active agent which alter heart function (such as epinephrine), parasympathetic stimulation (such as vagal stimulation), injection of liquids increasing blood volume (such as colloidal plasma substitutes) or exposure to enhanced levels of respiratory gases.

Figure 1:
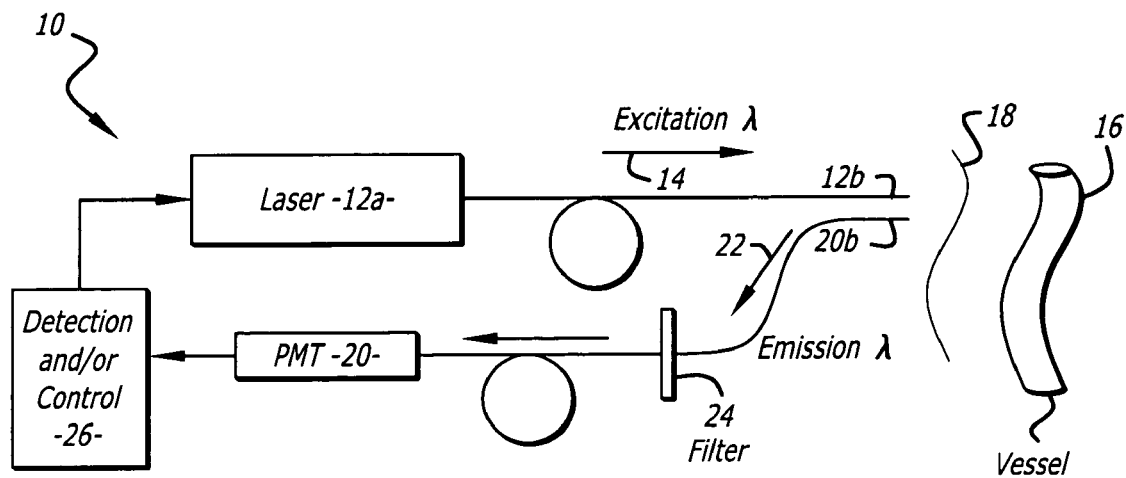
FIG. 1 is a diagrammatic depiction of an example of one embodiment of the system of the present invention.
Figure 2:
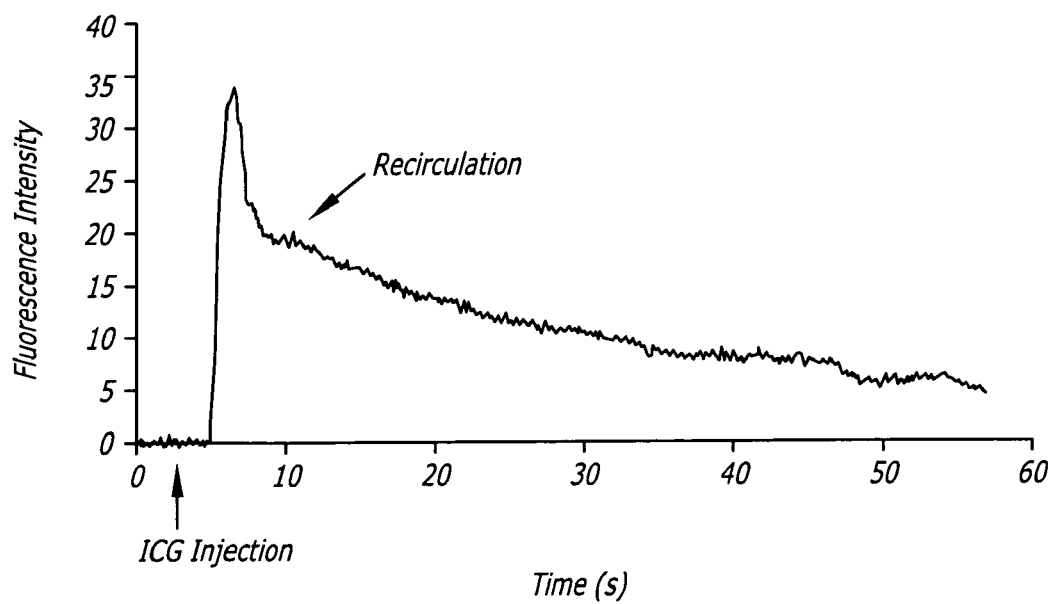
FIG. 2 is a fluorescence intensity curve generated using one embodiment of the present invention.
Figure 3:
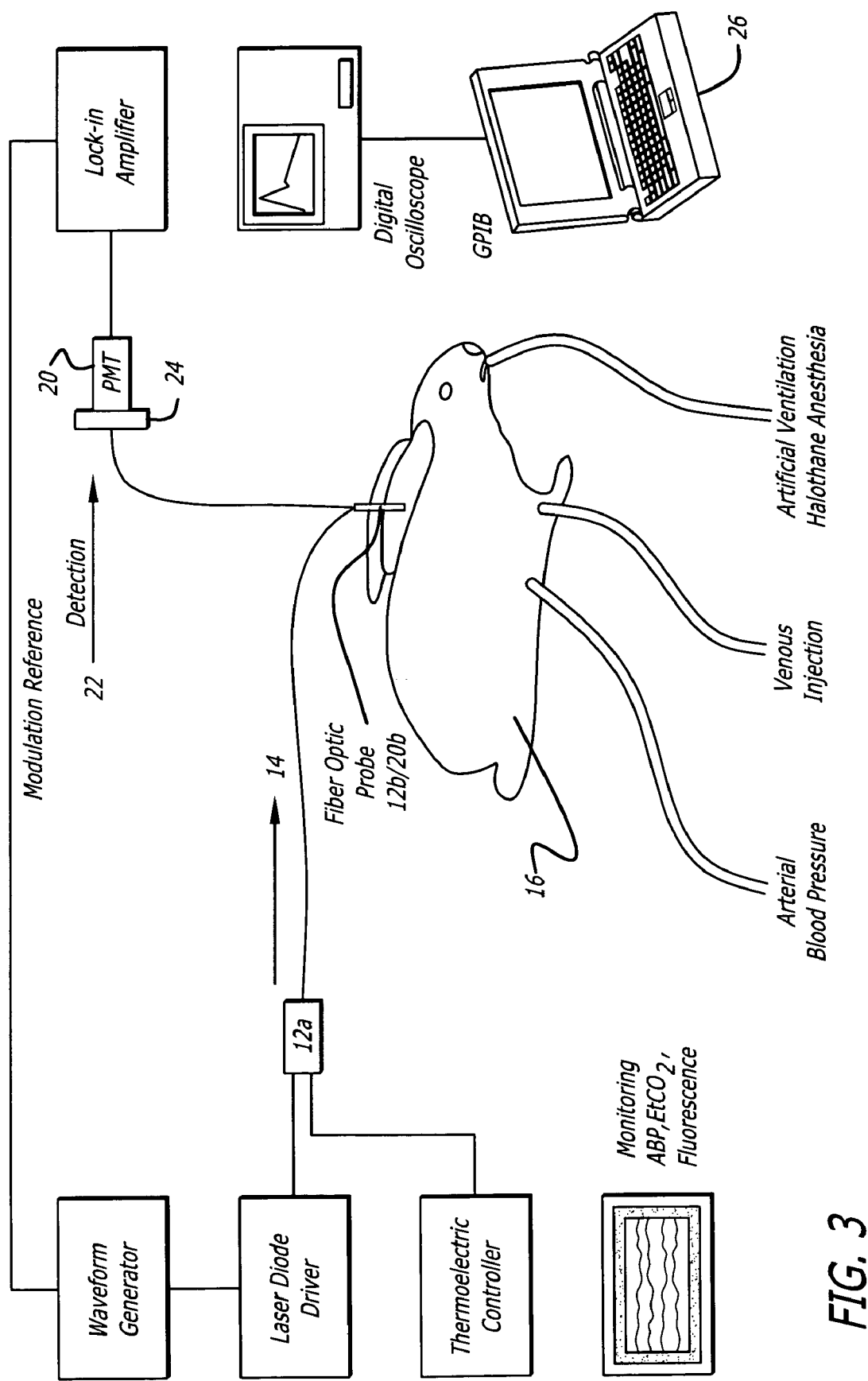
FIG. 3 is a diagrammatic depiction of an example of one embodiment of the present invention having a photodetector positioned on the ear skin surface.

A schematic of one embodiment of a system 10 useful in the present invention is shown in FIG. 1. The system comprises an illumination source 12a here a 775 nm laser selected to emit an excitation wavelength of light 14 which maximally excites ICG, the indicator selected. Here the illumination source 12a is positioned proximately to the subject 16, such that the excitation wavelength of light 14 is shone transdermally onto the indicator circulating in the bloodstream. The system also comprises a photodetector 20 placed in proximity to the subject's skin surface 18 for detection of the indicator emission intensity 22. Optionally, a filter 24 may be used for isolating the peak wavelength at which the indicator emits, being about 830 nm. Finally, the photodetector 20 is operably connected to a microprocessor 26 for storing the electronic signals transmitted from the photodetector 20 over time, and generating the indicator concentration curve (FIG. 2). Optionally, the microprocessor 26 may regulate the illumination source to coordinate the excitation and detection of emissions from the indicator, for example using a modulation technique. The microprocessor may also comprise software programs for analyzing the output obtained from the detector 20 such that the information could be converted into values of cardiac output or blood volume, for example and/or displayed in the form of a user interface.

In order to demonstrate the utility of the invention, a non-invasive indicator detection system 10 of the invention was used to repeatedly monitor cardiac output. With reference to FIG. 1, a fiber optic 12b transmitted light from illumination source 12a to the subject's skin 18. A second fiber optic 20b, positioned near the skin 18 transmitted the emitted light to a photodetector 20. The indicator was intravenously injected. A body portion which included blood vessels near the surface of the skin, was irradiated with a laser. A characteristic fluorescence intensity/concentration curve was obtained upon excitation with laser light at about 775 nm and detection of the fluorescence at about 830 nm. From this information cardiac output and blood volume for the subject was calculated.

The system used for this method may comprise a variety of additional components for accomplishing the aims of this invention. For example, non-invasive detection is described for monitoring of indicators within the circulatory system of the patient. Modifications of the detectors to accommodate to various regions of the patient's body or to provide thermal, electrical or chemical stimulation to the body are envisioned within the scope of this invention. Also, calibration of the system may be automated by a computing system, such that a blood sample is drawn from the patient after administration of the indicator, concentration detected and compared with known standards and/or the emission curve. Also, software may be used in conjunction with the microprocessor to aid in altering parameters of any of the components of the system or effectuating the calculations of the cardiovascular parameters being measured. Further, software may be used to display these results to a user by way of a digital display, personal computer or the like.

The utility of the invention is further illustrated by the following examples, which are not intended to be limiting.

EXAMPLE 1

Experimental system and method. An implementation of the system and method of this invention was tested in rats. The excitation source was a 775 nm pulsed diode laser and the fluorescence was detected with a detector being a photomultiplier (PMT) with extended response in the near-infrared range of the spectrum (FIG. 1). Optic fibers were placed in close contact with the skin of the animal's ear for the excitation and detection of the indicator within the blood stream. After injection of a 100 µl bolus of ICG (0.0075 mg/ml) into the jugular vein of a rat, the fluorescence intensity trace (indicator concentration recording) was measured transcutaneously at the level of the rat's ear using reflection mode detection of emissions (FIG. 2).

Calculation of blood volume and cardiac output. The initial rapid rise and rapid decay segments of the fluorescence intensity trace represent the first pass of the fluorescent indicator in the arterial vasculature of the animal. Such a waveform is characteristic of indicator dilution techniques. This portion of the recording is analyzed with one of several known algorithms (i.e. Stewart Hamilton technique) to compute the "area under the curve" of the fluorescence intensity trace while excluding the recirculation artifact. Here, the initial portion of the fluorescence trace y(t) was fitted with a model equation $y(t) = y_0 t^\alpha \exp(-\beta t)$ which approximates both the rising and descending segments of the trace. This equation derived from a "tank-in-series" representation of the cardiovascular system has been found fit well the experimental indicator dilution recordings. The numerical parameters of the fit were determined from the approximation procedure, and then the "area under the curve" was computed by numeric integration and used to find the cardiac output with the known formula:

$$Q = \frac{m}{\int_0^\infty C(t)\,dt} = \frac{\text{amount injected}}{\text{area under the curve}}$$

Back extrapolation of the slow decay segment of the fluorescence intensity trace to the instant when ICG is first detected in the blood (time 0) yields the estimated concentration of ICG mixed in the whole circulating blood volume. By dividing the amount of injected ICG by this extrapolated ICG concentration at time 0, the circulating blood volume was computed.

Calibration methods. Indicator concentration C(t) was computed from the fluorescence y(t) using one of two calibration methods. Transcutaneous in vivo fluorescence was calibrated with respect to absolute blood concentrations of ICG, using a few blood samples withdrawn from a peripheral artery after bolus dye injection of ICG. The blood samples were placed in a fluorescence cell and inserted in a tabletop fluorometer for measurement of their fluorescence emission. The fluorescence readings were converted into ICG concentrations using a standard calibration curve established by measuring with the tabletop fluorometer the fluorescence of blood samples containing known concentrations of ICG.

An alternative calibration procedure which avoids blood loss uses a syringe outfitted with a light excitation—fluorescence detection assembly. The syringe assembly was calibrated once before the cardiac output measurements by measuring ICG fluorescence in the syringe for different concentrations of ICG dye in blood contained in the barrel of the syringe. During the measurement of cardiac output, a blood sample was pulled in the syringe during the slow decay phase of the fluorescence trace, that is the phase during which recirculating dye is homogeneously mixed in the whole blood volume and is being slowly metabolized. The fluorescence of that sample was converted to concentration using the syringe calibration curve and then related to the transcutaneous fluorescence reading. So long as the ICG concentrations in blood remain sufficiently low (<0.001 mg/ml), a linear relationship can be used to relate fluorescence intensity to concentration.

Either one of these calibration methods can be developed on a reference group of subjects to produce a calibration nomogram that would serve for all other subjects with similar physical characteristics (i.e., adults, small children etc.). This is advantageous over prior methods at least in that an additional independent measurement of the blood hemoglobin concentration for computation of the light absorption due to hemoglobin is not required.

EXAMPLE 2

Figure 4:
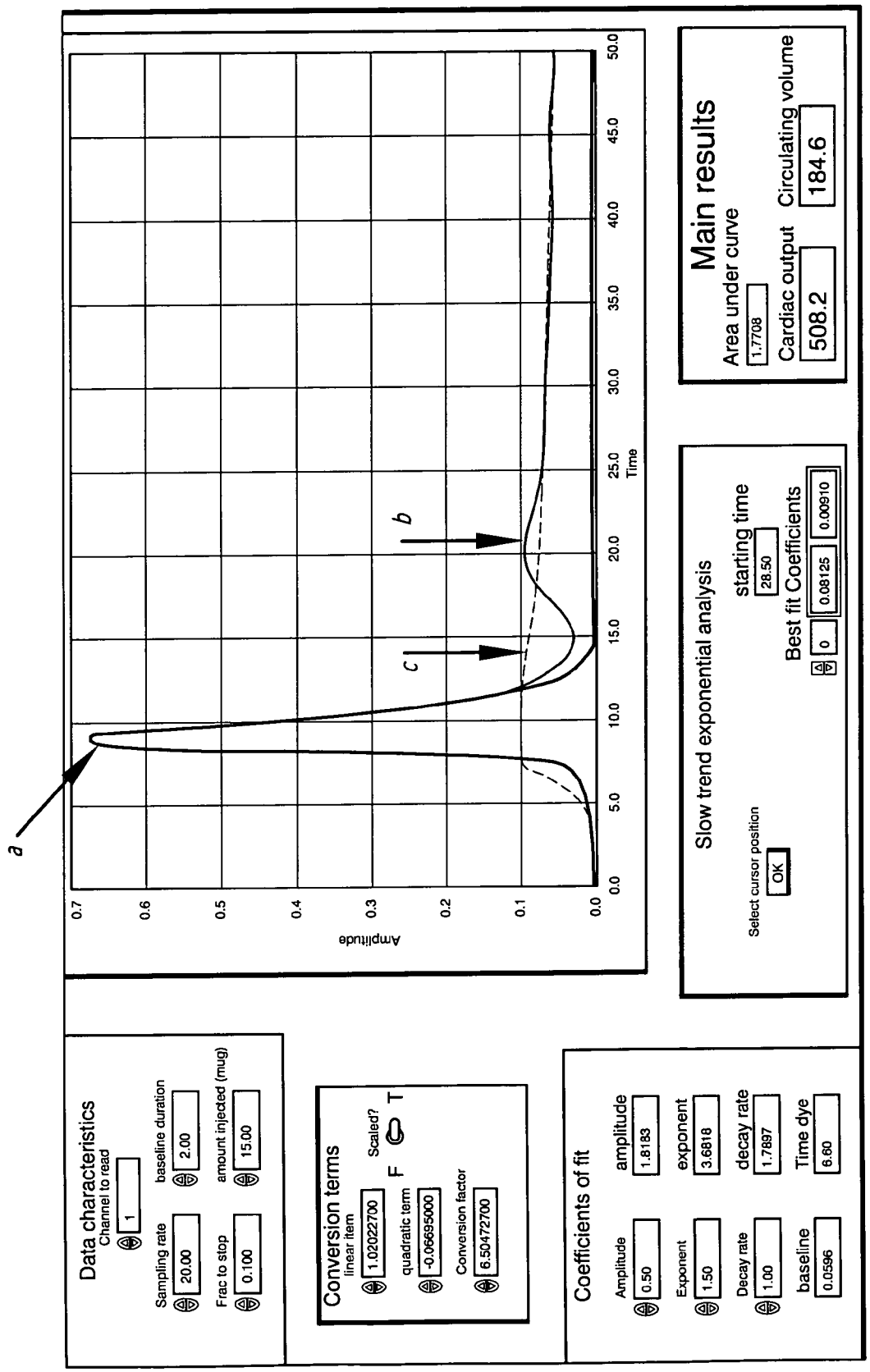
FIG. 4 is a diagrammatic depiction of a user interface of a cardiac output computer program useful in conjunction with this invention. The interface may depict information regarding values measured and converted from fluorescence to concentration, and parameters of the curve fit for the values obtained using the method or system.

A. A sample method and system for measuring cardiac output and blood volume. Experiments have been performed in New Zealand White rabbits (2.8-3.5 Kg) anesthetized with halothane and artificially ventilated with an oxygen-enriched gas mixture ($Fi_{O2}$~0.4) to achieve a $Sa_{O2}$ above 99% and an end-tidal $C_{O2}$ between 28 and 32 mm Hg (FIG. 4). The left femoral artery was cannulated for measurement of the arterial blood pressure throughout the procedure. A small catheter was positioned in the left brachial vein to inject the indicator, ICG. Body temperature was maintained with a heat lamp.

Excitation of the ICG fluorescence was achieved with a 780 nm laser (LD head: Microlaser systems SRT-F780S-12) whose output was sinusoidally modulated at 2.8 KHz by modulation of the diode current at the level of the laser diode driver diode (LD Driver: Microlaser Systems CP 200) and operably connected to a thermoelectric controller (Microlaser Systems: CT15W). The near-infrared light output was forwarded to the animal preparation with a fiber optic bundle terminated by a waterproof excitation-detection probe. The fluorescence emitted by the dye in the subcutaneous vasculature was detected by the probe and directed to a 830 nm interferential filter (Optosigma 079-2230) which passed the fluorescence emission at 830±10 nm and rejected the retro-reflected excitation light at 780 nm. The fluorescence intensity was measured with a photomultiplier tube (PMT; such as Hamamatsu H7732-10MOD) connected to a lock-in amplifier (Stanford Research SR 510) for phase-sensitive detection of the fluorescence emission at the reference frequency of the modulated excitation light. The output of the lock-in amplifier was displayed on a digital storage oscilloscope and transferred to a computer for storage and analysis.

In most experiments, one excitation-detection probe was positioned on the surface of the ear arterialized by local heating. In some studies, the laser emission beam was separated in two beams with a beam splitter and directed to two measurement sites (ear skin and exposed right femoral artery). Two detection systems (PMT+lock in amplifier) were used for measurement of the fluorescence dilution traces from the two sites. In all experiments, a complete record of all experimental measurements (one or two fluorescence traces, arterial blood pressure, end-tidal Co2, Doppler flow velocity) was displayed on line and stored for reference.

Calculations. A LabView program was used to control the oscilloscope used for sampling the fluorescence dilution curves, transfer the data from the oscilloscope to a personal computer and analyze the curves online for estimation of the cardiac output and circulating blood volume. As shown on the program user interface (FIG. 5), the measured fluorescence dilution trace (a) is converted to ICG blood (b) using the calibration parameters estimated as described in the next section of this application and fitted to a model: $C(t)=C_0 t^\alpha \exp(-\beta t)$.

The model fit (white trace) is performed from the time point for which the fluorescent ICG is first detected to a point on the decaying portion of the trace that precedes the appearance of recirculating indicator (identified from the characteristic hump after the initial peak in the experimental trace). The model equation is used to estimate the "area under the curve" for the indicator dilution trace. The theory of indicator dilution technique predicts that the area under the concentration curve is inversely proportional to the cardiac output (Q): $m/\int_0^\infty C(t)dt$.

where m is the mass amount of injected indicator and c(t) is the concentration of indicator in the arterial blood at time t. The program also fits the slow decaying phase of the measurement to a single exponential to derive the circulating blood volume from the value of the exponential fit at the time of injection. For the experimental ICG trace shown in FIG. 4, the estimated cardiac output is 509 ml/min and the circulating blood volume is 184 ml, in the expected range for a 3 Kg rabbit. This computer program is advantageous in that it improved the ability to verify that the experimental measurements are proceeding as planned or to correct without delay any measurement error or experimental malfunction.

Indicator dosage. In this experiment is was found that a dose of about 0.015 mg injected ICG was optimal in this animal to allow for detection of an intense fluorescence dilution curve and at the same time rapid metabolic disposal of the ICG. Further, with this small dose cardiac function measurements could be performed at about intervals of less than about every 4 minutes.

Detector placement. Defined fluorescence readings were obtained by positioning the detection probe above the skin surface proximate to an artery or above tissue, such as the ear or the paw arterialized by local heating.

B. Calibration of transcutaneous indicator intensity and circulating indicator concentration.

Calibration of the transcutaneous fluorescence intensity measured at the level of the animals' ear as a function of ICG concentration in blood was performed as follows. A high dose of ICG (1 mg) was injected intravenously and equilibrated homogeneously with the animal's total blood volume in about a one minute period. At equilibrium, the blood ICG concentration resulting from this high dose is several times larger than the peak ICG concentration observed during the low dose ICG injections (0.015 mg) used to measured cardiac output. In this way, a calibration curve was created that accommodated the full range of ICG concentrations observed during the cardiac function measurements.

As the liver metabolizes ICG, the blood ICG concentration decreases back to 0 in about 20 minutes. During that time period, 5 to 8 blood samples (1.5 ml) were withdrawn from the femoral artery and placed in a precalibrated blood cuvette. The fluorescence intensity of the blood in the cuvette was converted to a measurement of concentration using the known standard curve of fluorescence intensity versus ICG concentration established for the cuvette. ICG fluorescence was measured at the level of the ear at the exact time of the blood sample withdrawal. Because ICG is homogeneously equilibrated in the animal's blood volume, when the blood samples are withdrawn, the fluorescence intensity measured at the level of the ear corresponds directly to the ICG blood concentration at the time of the measurement and therefore the ICG concentration determined from the cuvette reading. As this example shows, transcutaneous ICG fluorescence is proportional to blood ICG concentration such that a single blood withdrawal can suffice to find the proportionality factor between the two quantities.

Figure 5:
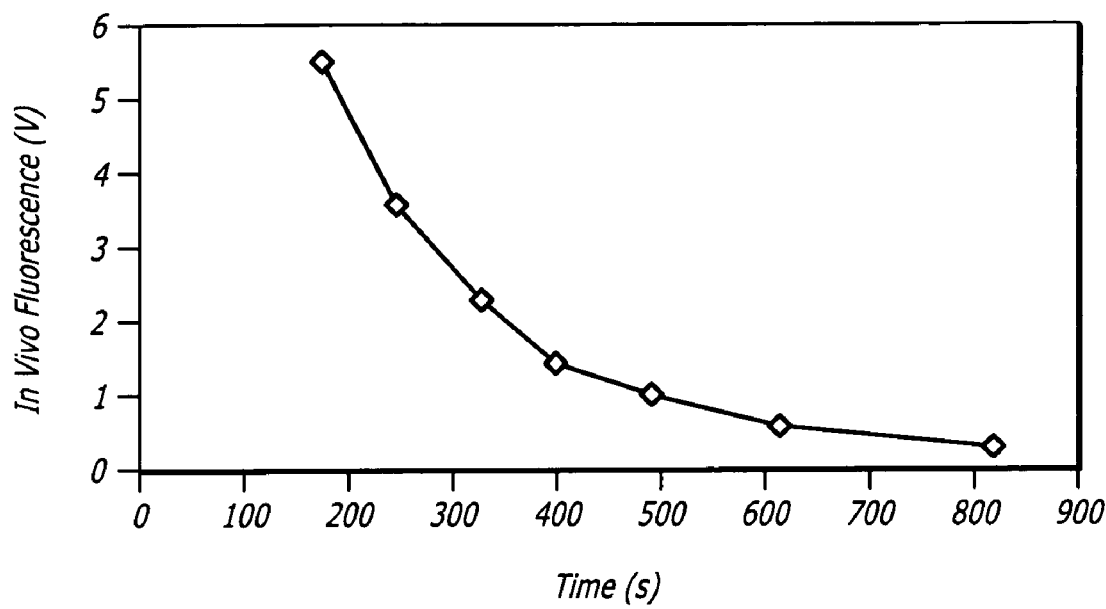
FIG. 5 is a depiction of a decay of fluorescence intensity curve as a function of time following injection of a 1 mg dose of ICG.
Figure 6:
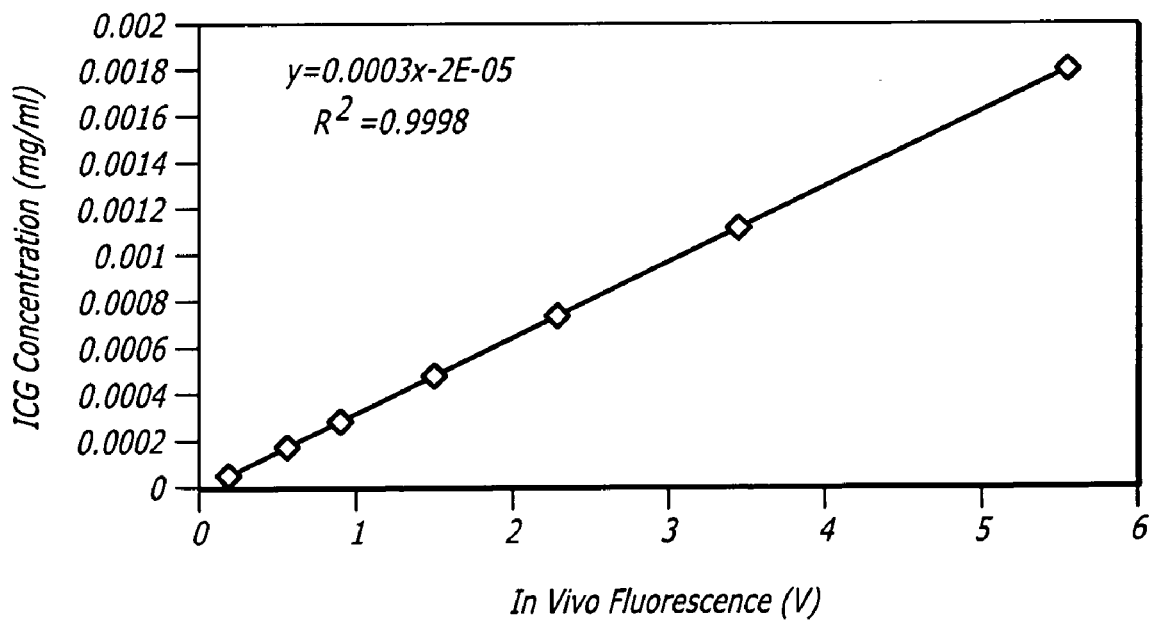
FIG. 6 is a depiction of a calibration curve for blood ICG concentration as a function of transcutaneous ICG fluorescence.

As shown in FIG. 5, the transcutaneous ear fluorescence intensity (in V) as a function of time (in s) after the high dose (1 mg) ICG injection during the calibration sequence. FIG. 5 shows the characteristic first order exponential decay of ICG in blood as the dye is being metabolized. FIG. 6 shows the ICG concentration (in mg/ml) as a function of the in vivo fluorescence for the same example and the same time points. For the range of concentrations used in these studies, ICG concentration and transcutaneous fluorescence were linearly related. The calibration line passes through the origin of the axes since there is no measured fluorescence when the ICG blood concentration is 0.

Thus, a simple proportionality factor exists between blood ICG concentration and transcutaneous fluorescence. This feature of the fluorescence dilution technique measuring light emission is advantageous over the conventional dye dilution technique based on ICG absorption which requires light absorption caused by ICG to be separated from light absorption by tissue and blood. After the proportionality factor is determined, ICG fluorescence dilution profiles can only then be converted into concentration measurements for computation of the cardiac output using the indicator-dilution equation.

Results of cardiac output measurements. Calibrated cardiac output readings have been obtained in 8 animals (body wt: 3.0±0.2 Kg). The following table lists the values during baseline conditions. The values are presented as the mean±standard deviation of three consecutive measurements obtained within a 15 min period.

TABLE 1.

TABLE 1

| Exp. | Cardiac output (ml/min) |
|---|---|
| 1 | 530 ± 15 |
| 2 | 500 ± 17 |
| 3 | 370 ± 12 |
| 4 | 434 ± 16 |
| 5 | 481 ± 6 |

The average for the five experiments (463 ml/min) is in order of reported cardiac outputs (260-675 ml/min) measured with ultrasound or thermodilution techniques in anesthetized rabbits (Preckel et al. Effect of dantrolene in an in vivo and in vitro model of myocardial reperfusion injury. Acta Anaesthesiol Scand, 44, 194-201, 2000. Fok et al. Oxygen consumption by lungs with acute and chronic injury in a rabbit model. Intensive Care Med, 27, 1532-1538, 2001). Basal cardiac output varies greatly with experimental conditions such as type of anesthetic, duration and depth of anesthesia, leading to the wide range of values found in the literature. In this example, the variability (standard deviation/mean) of the calculated cardiac output with fluorescence dilution is ~3% for any triplicate set of measurements which compares favorably with the reported variability for the thermodilution technique (~5-10%).

C. Comparison of measurements obtained by fluorescence dilution cardiac output method via transcutaneous measurement and subcutaneous measurement.

Experimental methodology. The experimental preparation described in the preceding section (Example 2) includes two measurement sites for the fluorescence dilution traces: a transcutaneous site at the level of the ear central bundle of blood vessels and the exposed femoral artery. The ear vasculature is arterialized by local heating. With this preparation, the cardiac output estimates obtained from the peripheral non-invasive (transcutaneous) measurement site were compared with estimates obtained by interrogating a major artery.

The intensity of the fluorescence signal at the level of the exposed femoral artery during the slow metabolic disappearance phase of the injected ICG is compared to the calibrated ear fluorescence measurement to derive a calibration coefficient (arterial ICG fluorescence into ICG blood concentration). In this way cardiac output estimates expressed in ml/min were derived from the two sites.

Figure 8:
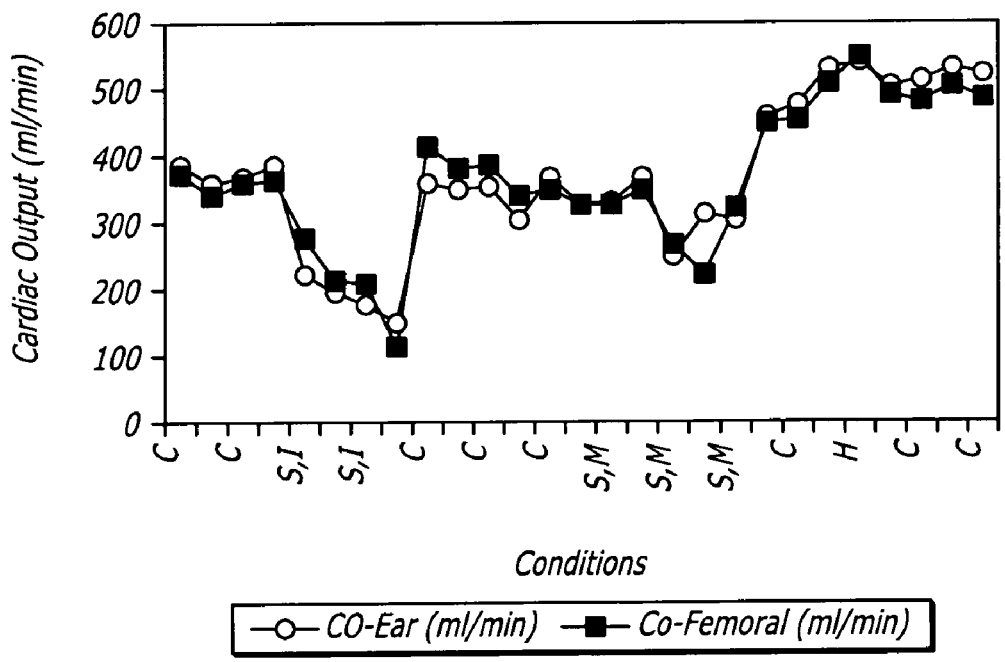
FIG. 8 is a depiction of cardiac output measurements derived from sites on the ear surface and on the exposed femoral artery during one experiment.

Results. FIG. 8 shows the time course of the cardiac output measurements obtained from the ear site and from the exposed femoral artery in a representative experiment during control conditions (C), intense then mild vagal stimulation (S,I and S,M), and post-stimulation hyperemia (H). Near-identical estimates of the cardiac output are obtained from the two sites during all phases of the study.

The relationship between cardiac output derived from measurement of the fluorescence dilution curve at the level of the skin surface ($Co_{skin}$, in ml/min) and at the level of the exposed femoral artery ($Co_{fem}$, in ml/min) was investigated. The linear relationships between the two measures are summarized in the table below:

TABLE 2

| Exp. | Linear regression | Regression Coef. | Number measurements |
|---|---|---|---|
| 1 | $Co_{skin} = 0.65(\pm 0.11) * C_{Ofem} + 145.0(\pm 54.0)$ | 0.81 | 22 |
| 2 | $Co_{skin} = 1.01(\pm 0.06) * C_{Ofem} + 2.0(\pm 22.0)$ | 0.96 | 27 |
| 3 | $Co_{skin} = 1.05(\pm 0.14) * C_{Ofem} - 56.0(\pm 54.0)$ | 0.91 | 13 |

The two measures of fluorescence cardiac output are tightly correlated. In the last two experiments, the slope of the regression line is not statistically different from 1.0 and the ordinate is not different from 0.0 indicating that the two measurements are identical. These observations suggest that fluorescence dilution cardiac output can be reliably measured transcutaneously and from a peripheral site of measurement that has been arterialized by local application of heat. Attenuation of the excitation light and ICG fluorescence emission by the skin does not prevent the measurement of well-defined dye dilution traces that can be analyzed to derive the cardiac output.

While the specification describes particular embodiments of the present invention, those of ordinary skill can devise variations of the present invention without departing from the inventive concept.

D. Comparison of measurements obtained by fluorescence dilution cardiac output method and doppler flow velocity technique.

Experimental methodology. The present method was compared with an ultrasonic Doppler velocity probe method to record cardiac output measurements. In this example the above procedure was modified in that, the animal's chest was opened with a median incision of the sternum and a 6 mm 20 MHz Doppler velocity probe was gently passed around the ascending aorta and tightened into a loop that fits snuggly around the aorta.

For detection of the fluorescent detection of the indicator, two illumination+detection fiber optic probes were used: one probe was placed on or above the ear middle vessel bundle and the other probe was placed in proximity to the dissected left femoral artery. Local heating to 44 degrees centigrade arterialized the ear vasculature.

Figure 7:
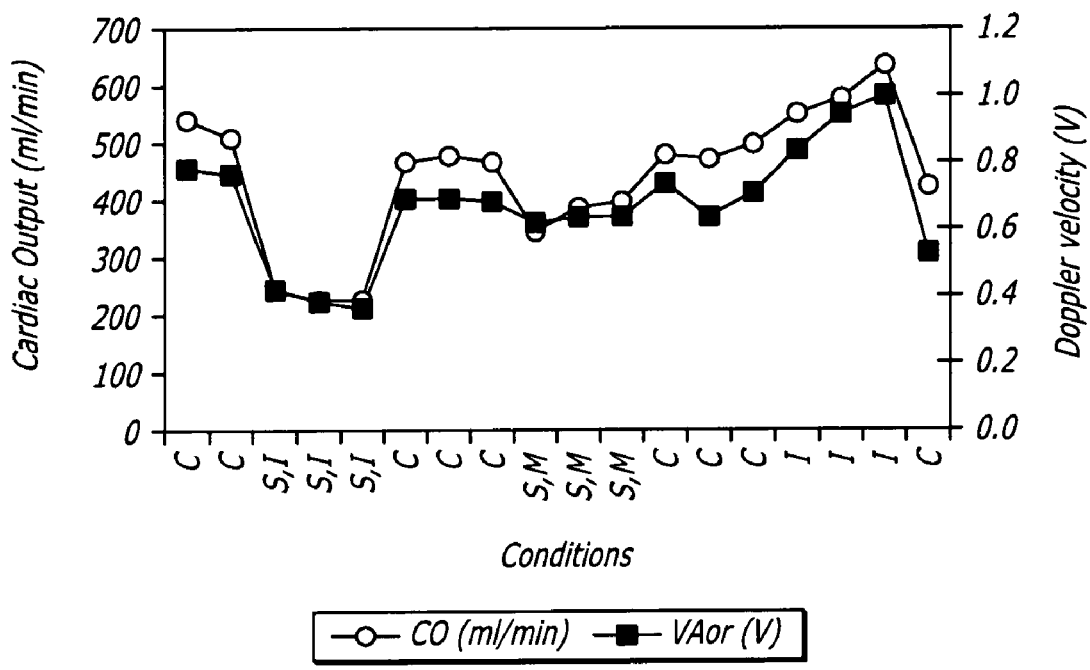
FIG. 7 is a depiction of cardiac output and aortic velocity measurements during one representative experiment.

In this example, two maneuvers were used to change the cardiac output from its control level: vagal stimulation, which reduces the cardiac output, and saline infusion, which increases the circulating volume and cardiac output. The right vagal nerve was dissected to position a stimulating electrode. Stimulation of the distal vagus results in a more or less intense decrease of the heart rate that depends on the stimulation frequency and voltage (1 ms pulses, 3 to 6 V, 10 to 30 Hz). The cardiac output and aortic flow velocity also decrease during vagal stimulation even though less markedly than the heart rate decreases because the stroke volume increases. Saline infusion at a rate of 15-20 ml/min markedly increases the cardiac output. FIG. 7 shows the time course of the cardiac output and aortic velocity measurements in one experiment including control conditions (C), intense then mild vagal stimulation (S,I and S,M), and saline infusion (I).

Results. There is consistent tracking of the Doppler aortic velocity by the fluorescence dilution cardiac output measurement. The relationship between fluorescence dilution cardiac output and aortic Doppler flow velocity was investigated in four rabbits. The linear relationships between fluorescence dilution cardiac output (CO, in ml/min) and aortic flow velocity signal ($vA_{or}$, not calibrated, in Volts) are summarized in the table:

TABLE 3

| Exp. | Linear regression | Regression Coef. | Measurements |
|---|---|---|---|
| 1 | $CO = 789(\pm 123) * v_{Aor} + 166(\pm 34)$ | 0.79 | 27 |
| 2 | $CO = 607(\pm 62) * v_{Aor} + 50(\pm 32)$ | 0.90 | 24 |
| 3 | $CO = 614(\pm 64) * v_{Aor} - 45(\pm 38)$ | 0.90 | 27 |
| 4 | $CO = 654(\pm 41) * v_{Aor} - 3(\pm 29)$ | 0.97 | 18 |

This data indicates that the fluorescence dilution cardiac output is highly correlated with aortic flow velocity as indicated by the elevated regression coefficient ($\geq 0.9$ in 3 experiments). Further, the slopes of the linear regression lines between fluorescence dilution cardiac output and aortic flow velocity are similar and statistically not different in the four studies. This suggests a constant relationship between the two variables across experiments. The ordinates of regression lines are not different from 0 in the last three experimental studies, which suggests absence of bias between the two measures of aortic flow.

The results above establish that fluorescence dilution cardiac output measured transcutaneously tracks the Doppler flow velocity measured in the ascending aorta.

We claim:

1. A method of measuring in absolute physical units cardiac output of a subject comprising:
   a) administering to a cardiovascular system of the subject a detectable amount of at least one indicator;
   b) applying a first wavelength of light for exciting the indicator within the cardiovascular system and causing the indicator to emit a second wavelength of light, wherein the second wavelength of light is fluorescence emitted by the indicator;
   c) measuring intensity of fluorescence emitted by the indicator in the cardiovascular system over a period of time using at least one photodetector proximately located to at a detection area of the subject;
   d) converting the measured intensity of the fluorescence over the period of time to a measured concentration of the indicator over a period of time using a known calibration curve that defines how the concentration of the indicator in the cardiovascular system varies as a function of the measured value of the intensity of the fluorescence;
   e) determining cardiac output of the subject in absolute units of volume over time based on the measured concentration of the indicator over the period of time.

2. The method of claim 1, wherein the determination of the cardiac output in absolute units of volume over time comprises at least one of curve fitting to a model equation or numerical integration.

3. The method of claim 2, wherein the method further comprises expressing the cardiac output as a function of either the subject's weight or the subject's surface area.

4. The method of claim 1, wherein the method further comprises back extrapolating the measured intensity of the fluorescence to near the instant of time of administration to determine a circulating blood volume in absolute physical units of volume.

5. The method of claim 1, wherein the photodetector is placed in at least one of a transdermal detection area, a subdermal detection area, a perivascular detection area or an endovascular detection area.

6. The method of claim 1, wherein the measuring further comprises detecting the intensity of the fluorescence by either transmission mode or reflection mode.

7. The method of claim 1, wherein steps a-e are repeated at a time interval to determine if the cardiac output for the subject has changed.

8. The method of claim 1, further comprising applying a stimulus to the subject and wherein steps a-e are repeated at a time interval to determine if the cardiac output for the subject has changed after exposure to the stimulus.

9. The method of claim 6, wherein the detection area is arterialized by application of heat or pharmacologically prior to the measuring the fluorescence at the detection area.

10. The method of claim 1, wherein the first wavelength of light is within the range of about 400 nm to about 1000 nm.

11. The method of claim 1, wherein the indicator is a chromophore or fluorophore emitting the fluorescence in a range from about 400 nm to about 1000 nm.

12. The method of claim 11, wherein the fluorophore is selected from the group comprising indocyanine green, fluorescein and rhodamine.

13. The method of claim 1 further comprising:
   removing a blood sample containing the indicator from the cardiovascular system; and
   determining the concentration of the indicator in the removed blood sample.

14. The method of measuring of claim 1 wherein the known calibration curve is defined for a specific site on the subject.

15. The method of measuring of claim 14 wherein the site is an ear of the subject.

16. The method of measuring of claim 14 wherein the site is a nose of the subject.

17. A system for measuring the cardiac output of a subject comprising:
   a) an illumination source configured to be positioned proximately to at least one blood vessel of a cardiovascular system of the subject for providing a first wavelength light for exciting an indicator within the cardiovascular system and causing the indicator to emit a second wavelength of light, wherein the second wavelength of light is fluorescence emitted by the indicator;
   b) a photodetector configured to be positioned proximate to the blood vessel of the cardiovascular system for detecting a magnitude of intensity of the fluorescence emitted from the indicator in the cardiovascular system and to generate electronic signals indicative of the detected magnitude of intensity of the fluorescence over a period of time; and
   c) a computing system configured to receive the electronic signals and to compute the cardiac output of the subject in absolute units of volume over time wherein the computer system:
      i. converts the electronic signals indicative of the detected magnitude of intensity of the fluorescence over the period of time to a measured concentration of the indicator over a period of time using a known calibration curve that defines how the concentration of the indicator in the cardiovascular system varies as a function of the measured value of the intensity of the fluorescence and
      ii. computes the cardiac output of the subject in absolute units of volume over time based on the measured concentration of the indicator over the period of time.

18. The system of claim 17, further comprising at least one fiber optic probe operably connected to the illumination source for guiding the first wavelength of light from the illumination source to the detection area.

19. The system of claim 17, further comprising at least one fiber optic probe operably connected to the photodetector for guiding the fluorescence from the detection area to the photodetector.

20. The system of claim 17, further comprising at least one lock-in amplifier operably connected to the illumination source for modulating the intensity of the first wavelength of light at a selected frequency, and operably connected to the photodetector for enhancing the detection of the fluorescence by the photodetector, only at the selected frequency of modulation.

21. The system of claim 17, wherein the photodetector is further configured to detect the magnitude of intensity of the fluorescence emitted from the indicator over a time period, forming a magnitude of intensity curve for the time period, and wherein the computing system is further configured to compute the cardiac output based on at least one of curve fitting to a model equation or a numerical integration.

22. The system of claim 21, wherein the computing system is further configured to express the cardiac output as a function of either the subject's weight or the subject's surface area.

23. The system of claim 17, wherein the computing system is further configured to compute circulating blood volume of the subject and wherein the photodetector is further configured to detect the magnitude of intensity of the fluorescence emitted from the indicator over a time period, forming a magnitude of intensity curve for the time period, and wherein the computing system is further configured to compute the blood volume by back extrapolating the electronic signal indicative of the fluorescence intensity to near the time of administration of the indicator in order to determine the circulating blood volume.

24. The system of claim 17, wherein the photodetector is further configured to be placed in at least one of a transdermal detection area, a subdermal detection area, a perivascular detection area or an endovascular detection area.

25. The system of claim 17, wherein the first wavelength of light is in the range of about 400 nm to about 1000 nm.

26. The system of claim 17, wherein the indicator is a chromophore or fluorophore capable of emitting the second wavelength of light in a range from about 400 nm to about 1000 nm.

27. The system for measuring of claim 17 wherein the known calibration curve is defined for a specific site on the subject.

28. The system for measuring of claim 27 wherein the site is an ear of the subject.

29. The system for measuring of claim 27 wherein the site is a nose of the subject.

30. A method of measuring blood volume in a subject comprising:
    a) administering a detectable amount of at least one indicator to a cardiovascular system of a subject;
    b) applying a first wavelength of light for exciting the indicator within the cardiovascular system and causing the indicator to emit a different second wavelength of light, wherein the second wavelength of light is fluorescence emitted from the indicator;
    c) measuring intensity of fluorescence emitted from the indicator in the cardiovascular system over a period of time using at least one photodetector proximately located to a detection area of the subject;
    d) converting the measured intensity of the fluorescence over the period of time to a measured concentration of the indicator over a period of time using a known calibration curve that defines how the concentration of the indicator in the cardiovascular system varies as a function of the measured value of the intensity of the fluorescence; and
    e) determining a magnitude of the blood volume in absolute units based on the measured concentration of the indicator over the period of time.

31. The method of measuring of claim 30 wherein the known calibration curve is defined for a specific site on the subject.

32. The method for measuring of claim 31 wherein the site is an ear of the subject.

33. The method of measuring of claim 31 wherein the site is a nose of the subject.

* * * * *